United States Patent [19]

Hauck et al.

[11] 4,033,971
[45] July 5, 1977

[54] CYCLOHEXANE TETROLS AND DERIVATIVES THEREOF

[75] Inventors: Frederic Peter Hauck, Somerville, N.J.; Joseph E. Sundeen, Yardley, Pa.

[73] Assignee: E. R. Squibb & Sons, Inc., Princeton, N.J.

[22] Filed: Nov. 18, 1975

[21] Appl. No.: 633,046

Related U.S. Application Data

[62] Division of Ser. No. 383,642, July 30, 1973, Pat. No. 3,936,465.

[52] U.S. Cl. .............. 260/293.72; 260/570.8 R; 260/570.9; 260/477.6; 260/487; 260/488 B; 260/488 J; 260/486 R; 260/477; 260/268 BC; 252/175; 424/325; 424/330; 424/263; 424/267; 424/274; 424/250; 424/309; 424/266; 260/326.8; 260/326.87; 260/293.56; 260/293.84; 260/295.5 R; 260/295 R; 260/295 F; 260/293.65; 260/326.2; 260/326.43; 260/326.5 R; 260/490; 260/563 R; 260/570.6

[51] Int. Cl.² .................................. C07D 211/32
[58] Field of Search .......... 260/293.65, 293.72, 260/326.8, 326.87

[56] References Cited

UNITED STATES PATENTS 3,936,465  2/1976  Hauck et al. ............... 260/293.65

*Primary Examiner*—Henry R. Jiles
*Assistant Examiner*—Robert T. Bond
*Attorney, Agent, or Firm*—Lawrence S. Levinson; Merle J. Smith; Burton Rodney

[57] ABSTRACT

The compounds of the invention have the formula

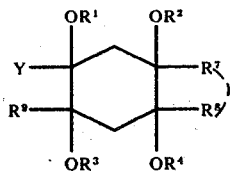

wherein
Y is a radical of the formula

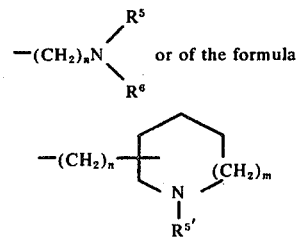

or of the formula wherein
($CH_2$) is a straight or branched chain alkyl radical, $n$ is 1–6, $m$ is 0 or 1 and $R^5$ is hydrogen, alkyl, arylalkyl, and $R^5$ and $R^6$ together with the nitrogen to which they are attached may be pyrrolidino, piperidino or N'-alkyl piperazino;

$R^1$, $R^2$, $R^3$ and $R^4$ may be the same or different and may be hydrogen; alkyl, trifluoromethyl; alkanoyl; haloalkanoyl; alkoxycarbonyl of the formula

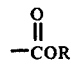

wherein
R is an alkyl radical; alkoxyalkyl; aminoalkanoyl of the formula

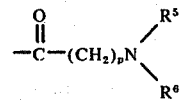

wherein
$R^5$ and $R^6$ are as previously defined and $p$ is 0—3; 2—, 3—, or 4—pyridylcarbonyl; phenyl; monosubstituted phenyl wherein the substituent is alkyl, alkoxy, hydroxy, nitro, amino, or dialkylamino; alkenoyl; or aroyl;

$R^9$ may be H, or a straight or branched chain alkyl radical of 1–6 carbon atoms;

$R^7$ and $R^8$ may be the same or different and may be hydrogen or alkyl, and $R^7$ and $R^8$ taken together with the carbon atoms bearing substituents $OR^2$ and $OR^4$ may form a cycloalkyl ring. These compounds have been found useful in the treatment of hypertension in mammalian species, as surface active agents, as in vivo antibacterial compounds and as water softeners.

6 Claims, No Drawings

CYCLOHEXANE TETROLS AND DERIVATIVES THEREOF

RELATED APPLICATION

This application is a division of application Ser. No. 383,642, filed July 30, 1973, now U.S. Pat. No. 3,936,465.

BACKGROUND OF THE INVENTION

The problem of hypertension is widely prevalent and while some progress has been made in its treatment, there is a need for more effective compounds, and for compounds which have fewer side effects.

OBJECTS OF THE INVENTION

It is an object of the present invention to provide new compounds which are effective in treating hypertension. A further object is to provide methods for the preparation of these compounds. Another object is to provide pharmaceutically acceptable compositions incorporating the compounds of the present invention. Still another object is to provide methods for the therapeutic administration of the compounds of the present invention. These and other objects of the present invention will be apparent from the following description.

SUMMARY OF THE INVENTION

The compounds of the invention have the formula

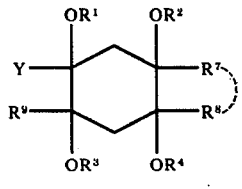

wherein
Y is a radical of the formula

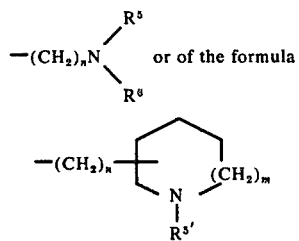 or of the formula

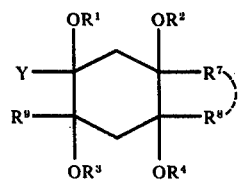

wherein $(CH_2)$ is a straight or branched chain alkyl radical, $n$ is 1–6, $m$ is 0 or 1 and $R^{5'}$ is hydrogen, alkyl of from 1 to 3 carbon atoms, arylalkyl and $R^5$, $R^5$ and $R^6$ together with the nitrogen atom to which they are attached may be pyrrolidino, piperidino or $N'$-alkyl piperazino wherein the alkyl radical has from 1 to 3 carbon atoms;

$R^1$, $R^2$, $R^3$ or $R^4$ may be the same or different and may be hydrogen; alkyl of from 1 to 4 carbon atoms; alkanoyl of from 1 to 4 carbon atoms, haloalkanoyl of from 1 to 4 carbons wherein the halogen may be F, Cl, Br or I; alkoxycarbonyl of the formula

wherein R is an alkyl radical of from 1 to 4 carbon atoms; alkoxyalkyl or benzyloxyalkyl wherein the alkoxy radical has from 1 to 3 carbons and the alkyl radical has from 1 to 3 carbons; aminoalkanoyl of the formula

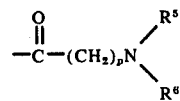

wherein $R^5$ and $R^6$ are as previously defined and $p$ is 0—3; 2-, 3-, or 4-pyridylcarbonyl; phenyl; monosubstituted phenyl wherein the substituent is alkyl of from 1 to 4 carbons, alkoxy of from 1 to 4 carbons, hydroxy, nitro, amino, or dialkylamino wherein each alkyl radical may have from 1 to 4 carbon atoms; or alkenoyl of 3 or 4 carbon atoms; or aroyl of the formula

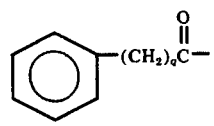

wherein $g$ is 0-3;

$R^9$ may be H or a straight or branched chain alkyl radical of 1–6 carbon atoms;

$R^7$ and $R^8$ may be the same or different and may be hydrogen or alkyl of from 1 to 4 carbons, and $R^7$ and $R^8$ taken together with the carbon atoms bearing substituents $OR^2$ and $OR^4$ may form a cycloalkyl ring having from 5 to 7 carbon atoms. These compounds have been found useful in the treatment of hypertension in mammalian species, as surface active agents, as in vivo anti-bacterial compounds and as water softeners.

DETAILED DESCRIPTION

The present invention relates to cyclohexane tetrol derivatives which have a lowering effect on blood pressure and are useful in the treatment of hypertension in mammalian species, for example, rats and dogs. In addition, the compounds of the invention are surface active agents, have anti-bacterial properties in vitro and are also useful as water softeners. A compound of the invention as well as its physiologically acceptable acid addition salts may be compounded according to conventional pharmaceutical practice in oral or parenteral dosage forms such as tablets, capsules, elixirs, injectables or powders for administration in dosage levels of from about 50 mg to about 400 mg per day, preferably from about 100 mg to about 200 mg per day, in 2 to 4 divided doses.

The compounds of the present invention have the general formula

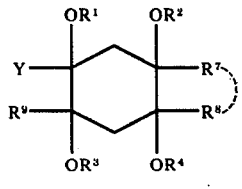

In the foregoing formula Y may be a radical of the formula

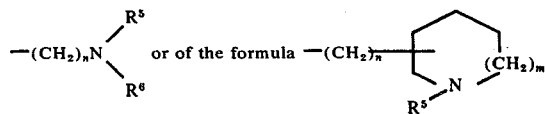

wherein (CH$_2$) is a straight or branched chain alkyl radical, $n$ is 1 to 6, $m$ is 0 or 1 and R$^5$ and R$^6$ are as previously defined. Examples of specific radicals for Y are the following:

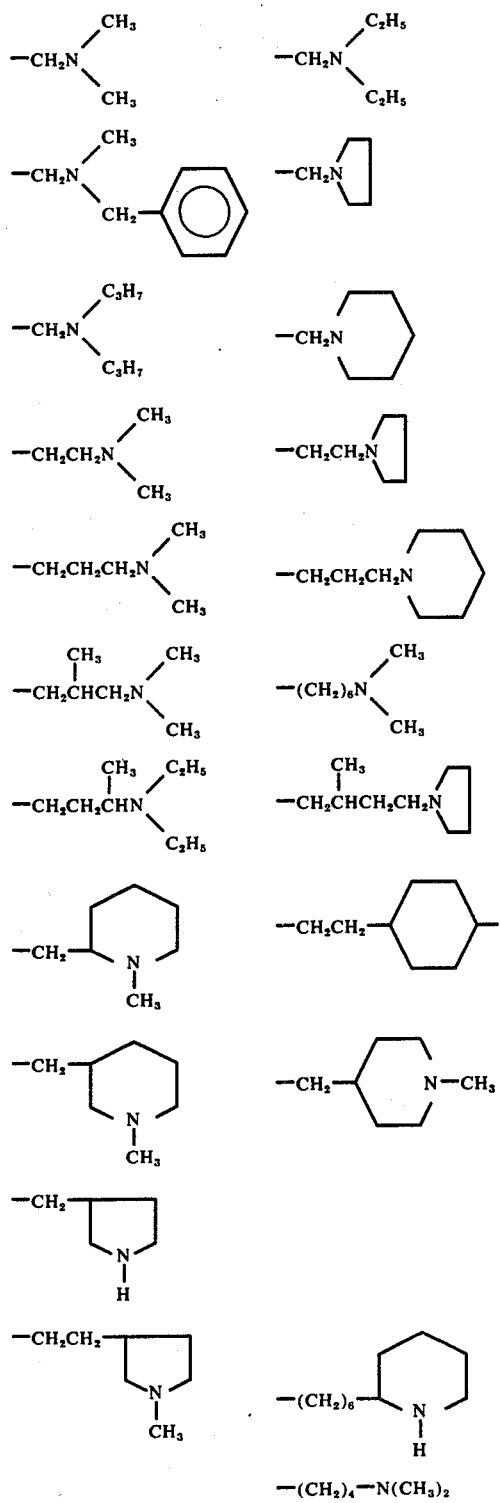

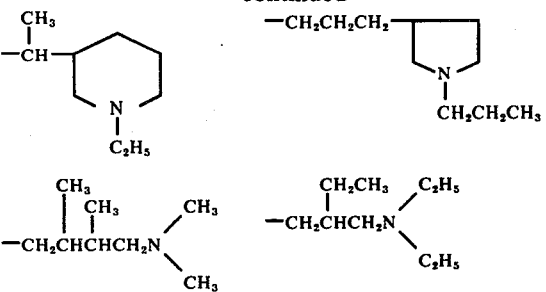

In the foregoing formula, R$^1$, R$^2$, R$^3$ and R$^4$ may be the same or different. Examples of specific radicals for each of R$^1$, R$^2$, R$^3$ and R$^4$ are the following: hydrogen; methyl, ethyl, n-propyl, i-propyl, n-butyl, i-butyl or t-butyl; trifluoromethyl; formyl, acetyl, propionyl, isopropionyl, butanoyl, isobutanoyl, or t-butanoyl; chloroacetyl, bromoacetyl, trifluoroacetyl, 2-bromopropionyl, 3-bromopropionyl, 2-chloropropionyl, 3-chloropropionyl, 2,3-dibromopropionyl, or 2,3-dichlorobutanoyl; methoxycarbonyl, ethoxycarbonyl, propoxycarbonyl, isopropoxycarbonyl, butoxycarbonyl, isobutoxycarbonyl or t-butoxycarbonyl; methoxyethyl, methoxypropyl methoxymethyl, ethoxymethyl, ethoxyethyl, ethoxypropyl, propoxymethyl, propoxyethyl, propoxypropyl, i-propoxymethyl, i-propoxyethyl, i-propoxypropyl, methoxyisopropyl, ethoxyisopropyl, propoxyisopropyl; amido, dimethylamido, diethylamido, dipropylamido, diisopropylamido, pyrrollidinocarbonyl, piperidinocarbonyl; 2-aminoacetyl, 3-aminopropionyl, 4-aminobutanoyl, dimethylaminoacetyl, diethylaminopropionyl, dimethylaminobutanoyl, diisopropylaminoacetyl; 2-, 3- or 4-pyridylcarbonyl; phenyl, o-tolyl, m-tolyl, p-tolyl, o-ethylphenyl, m-propylphenyl, p-butylphenyl; o-hydroxyphenyl, m-methoxyphenyl, p-ethoxyphenyl; o-nitrophenyl, m-nitrophenyl, p-aminophenyl; p-dimethylaminophenyl; o-allylphenyl or m-crotonylphenyl;

R$^7$ and R$^8$ may be hydrogen, methyl, ethyl, propyl i-propyl, butyl, sec-butyl, t-butyl or together may be

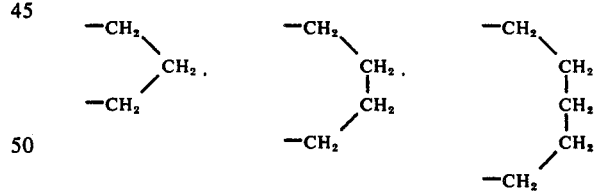

R$^9$ may be H, methyl, ethyl, propyl, i-propyl, butyl, i-butyl, t-butyl, amyl, neopentyl, isoamyl, 2-methylbutyl, hexyl, isohexyl, 2-methylpentyl, 3-methylpentyl, or 2-ethylbutyl.

The compound of the present invention may be prepared by the following general reaction sequence wherein Y, R$^1$, R$^2$, R$^3$, R$^4$, R$^7$, R$^8$ and R$^9$ are as previously defined, or wherein Y is an unsaturated precursor of Y:

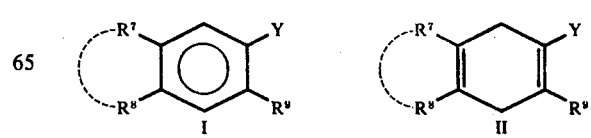

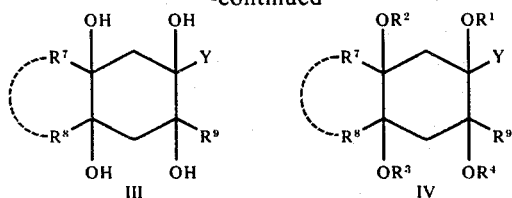

-continued

III
IV

The aromatic compound of formula I is converted to the cyclohexadienyl compound of formula II by means of a Birch reduction. The Birch reduction is carried out by reacting the compound of formula I with lithium in the presence of liquid ammonia, a proton source such as a lower alkanol and ethyl ether, as known to those skilled in the art. The compound of formula II is converted to the tetrol of formula III by treatment with excess $H_2O_2$ and formic acid, at about room temperature with cooling. After completion of the reaction, the mixture is rendered alkaline by treating with a base. The tetrol of formula III is converted to the compound of formula IV by treatment with the appropriate esterifying agent in the presence of $HClO_4$ or pyridine, with cooling in each case.

Alternatively, a solution of substituted cyclohexadiene of formula II (0.1 mol) is dissolved in about 150 ml of a carboxylic acid and treated in the cold portionwise with about 1 equivalent of a strong acid with a non-participating anion, i.e., one which does not open an epoxide, e.g., perchloric, sulfuric or nitric. The resulting solution of the salt is treated at temperatures of from about 10 to about 20° with at least about 2 equivalents of peracid corresponding to the carboxylic acid employed at temperatures of up to about 35°–40°. The mixture is stirred at from about 30° to about 55° for several hours, then cooled in ice and slowly diluted with ether to precipitate the salt of the partially acylated tetrol as an oil product. The product is washed with ether, cooled in a dry ice-acetone bath to about −30° and treated with the appropriate acid anhydride followed by a small amount of an acid with a non-participating anion, i.e., one which does not open an epoxide, e.g., perchloric, sulfuric or nitric. After about 1 hour at a temperature of from about −30° to about −15°, the mixture is held overnight at a temperature of from about −15° to about 0°. Excess acylating agent is then destroyed at temperatures of from about −10° to about 0° by addition of excess methanol. The mixture is then poured into cold concentrated ammonia and the product extracted into dichloromethane, treated and freed of solvent. The product is then purified by recrystallization or chromatography.

The compounds of the present invention include the stereoisomers, optical isomers and conformers having the structural formula IV. The compounds of the present invention have a lowering effect on blood pressure and are useful in the treatment of hypertension in mammalian species, e.g., dogs and rats. In addition the compounds of the present invention are useful surface active agents, as in vitro antibacterial compounds and as water softeners. A compound of formula IV as well as its physiologically acceptable salts may be compounded according to pharmaceutical practice in oral or parenteral dosage from such as tablets, capsules, elixirs, injectables or powders for administration in quantities of from about 50 mg to about 400 mg per day, preferably from about 100 mg to about 200 mg per day, in 1 dose or from 2 to 4 divided doses.

The following examples illustrate the present invention without, however, limiting the same thereto. All temperatures are given in degrees Centigrade.

EXAMPLE 1

1,2-trans-4,5-trans-1-[4-(Dimethylamino)butyl]-2-methyl-1,2,4,5-cyclohexanetetrol, tetraacetate ester From 300 g (1.9 moles) of dimethylaminopropyl chloride hydrochloride there is obtained approximately 200 ml of free base by basifying an 800 ml solution with solid sodium carbonate and separating the layers. The liquid is dried ½ hr over sodium carbonate, 3 volumes of ether added, and the solution filtered.

Magnesium turnings (36 g, 1.5 moles) are placed in a 5 liter flask under nitrogen. Ether (100 ml) and 5 ml of methyl iodide are added and the ensuing reaction allowed to subside completely. Then the solution of the chloride is added to maintain vigorous reflux. After the addition (45 min) the mixture is stirred another 15 min, then treated with a solution of o-tolualdehyde (100 g, 0.83 moles) in 400 ml of ether at a rate to maintain vigorous reflux. The mixture is stirred 1 hr, then treated with saturated ammonium chloride until granular and additional saturated ammonium chloride causes only slight reflux. The salts are filtered and washed with ether. Evaporation gives 96 g (60%) of 2-[(4-dimethylamino-1-hydroxy)-1-butyl]toluene, showing no carbonyl absorption in the ir spectrum.

The Grignard adduct (96 g, 0.5 moles) is taken up in 800 ml of glacial acetic acid and treated with 300 ml of concentrated HCl. The mixture is heated to reflux for 15 minutes, cooled and evaporated to an oil. This is taken up in 1 liter of water, extracted with methylene chloride, and the aqueous layer basified with 10% sodium hydroxide. Extraction with dichloromethane, drying (potassium carbonate) and evaporation gives an oil. This is taken up in 400 ml of ether and added to 2.5 liters of liquid ammonia. Then 50 g of lithium are added over 40 minutes, the mixture stirred ¾ hr, and then absolute ethanol added over 2 hrs to discharge the blue color. The ammonia is evaporated with the aid of a water bath, and water and ether added with ice cooling. The aqueous layer is separated and reextracted with ether. The organics are dried over potassium carbonate and evaporated to 77 g (87%) of 1-[(4-dimethylamino)-1-butyl]-2-methyl-3,6-dihydrobenzene.

The diene (77 g, 0.44 moles) is taken up in 1.5 liters of 88% formic acid and treated over 15 minutes with 100 ml of 30% hydrogen peroxide, T ≤ 35° C with cooling. The solution is stirred 16 hrs at room temp, 500 ml of water added, and evaporated in vacuo to an oil. This is dissolved in 1 liter of 95% ethanol and made strongly basic with 20% sodium hydroxide. This is heated on a steam cone for 1.5 hrs, cooled and extracted with 2.5 liters of ether. The organics are dried (magnesium sulfate) and evaporated, then boiled with benzene to remove water and allowed to cool in 1.5 liters of benzene. The supernatant is poured off and the 50 g residue chromatographed on 800 g Activity IV basic alumina in chloroform. With 2.5 liters of chloroform there are eluted 10 g of material. The next four fractions in 5% methanol give 38 g (34%) single spot (by TLC) tetrol as an oil.

A 4.5 g (0.017 mole) sample of tetrol is taken up in 100 ml of acetic anhydride and 2 ml of acetic acid, cooled in dry ice-acetone, and treated with 3 ml of 70% perchloric acid. After standing overnight at −15° C, 60 ml of methanol are added over ½ hr with ice-acetone cooling. The mixture is poured into ice-ether-ammonia, the layers separated and the aqueous layer reextracted with ether. The organics are dried (magnesium sulfate) and treated with several portions of benzene with evaporation to dryness after each addition. The crude tetraacetate solidifies. The solid is taken up in 150 ml of hot hexane, treated with Darco, filtered hot and cooled to room temp. In 2 hrs the solid is filtered and dried at 60° C, 0.1 mm Hg for 20 hrs, over $P_2O_5$ and paraffin to give 3.7 g (50%), mp 90°–93° C.

EXAMPLE 2

1,2-trans-4,5-trans-1-[4-(Dimethylamino)butyl]-2-methyl-1,2,4,5-cyclohexanetetrol On standing the oily tetrol prepared in example 1 crystallizes from acetonitrile. A 3.5 g sample is taken up in 100 ml of methanol and 150 ml of hot ethyl acetate, treated with Darco, filtered and concentrated to 80 ml on a steam cone. Cooling and seeding with tetrol gives, after 24 hrs, 1.3 g, mp 141°–143° C.

EXAMPLE 3

1,2-trans-4,5-trans-1-[3-(Dimethylamino)propyl]-2-methyl-1,2,4,5-cyclohexanetetrol, tetraacetate ester To 25 g (0.19 moles) of o-methyl acetophenone in a mixture of 55 ml of benzene and 55 ml of nitrobenzene [J. Org. Chem. 10, 259 (1945)] is added 11 g (0.38 moles) paraformaldehyde, 16 g (0.2 moles) of dimethylamine hydrochloride, and 0.75 ml of concentrated hydrochloric acid. The mixture is heated to reflux under a water separator, and 6 ml of water is collected over 2 hrs. The clear yellow solution is cooled and the solid mass triturated with benzene, filtered and washed with ether to give the Mannich base hydrochloride, 41 g (99%).

The above solid is dissolved in 200 ml of water, extracted twice with dichloromethane (discard), then basified with 10% sodium hydroxide and extracted with 500 ml of benzene. The solution is clarified by filtering through a paper towel, and evaporated to 38 g of the free base, containing some benzene. This is taken up in 250 ml of ether and added over 5 min. to 2.0 g of lithium aluminum hydride in 200 ml of ether. After stirring ½ hr the mixture is quenched with water until white, filtered and washed with ether, and evaporated to the oily alcohol. This is taken up in 600 ml of glacial acetic acid, treated with 200 ml of concentrated HCl, and refluxed for 20 minutes. Evaporation in vacuo affords an oil which is dissolved in 500 ml of water and basified with 10% sodium hydroxide. The mixture is extracted with 500 ml of dichloromethane, benzene is added to the organic phase and the solution evaporated to yield 26 g (79%) of the unsaturated amine.

The 26 g (0.15 moles) of amine is taken up in 350 ml of ether, filtered, then added to 1.5 liters of liquid ammonia. Lithium ribbon (27 g, 3.9 moles) is added over 15 min, the mixture stirred 2 hrs, then made colorless with absolute ethanol over 2 hrs. After the ammonia has evaporated overnight, water (1 liter) is added with ice cooling, and the mixture extracted with 1.5 liters of ether. Drying (potassium carbonate) and evaporation gives 22 g (83%) of 3,6-dihydro-2-methyl-dimethylaminopropylbenzene.

The diene (22 g, 0.12 moles) in 800 ml of 97% formic acid is treated dropwise with 50 ml of 30% hydrogen peroxide (0.44 moles) maintaining T=35°–40° C. After standing at room temperature overnight the mixture is diluted to 2 liters with water and stripped to an oil in vacuo. Ethanol (500 ml) and enough caustic is added to basify strongly, and the mixture is heated for 1 hr on a steam bath. Cooling, extraction with 1.5 liters of ether and 0.5 liters of ethyl acetate, drying (magnesium sulfate), addition of benzene (300 ml) and evaporation gives 14 g of crude tetrol. chromatography on 200 g of Activity IV basic alumina in chloroform (600 ml) and then 5% methanol in chloroform brings out 5.3 g of single spot (by TLC) tetrol (17%).

A 2.2 g (0.009 mole) sample of tetrol in 100 ml of acetic anhydride cooling in a Dry Ice-acetone bath is treated with 2 ml of 70% perchloric acid, then allowed to come to −15° C overnight. With ice-acetone cooling, 70 ml of methanol are added over ½ hr, and the reaction poured into ice-ammonia and extracted with chloroform. Drying (magnesium sulfate), addition of benzene and evaporation gives 3.7 g (100%) crude solid 1,2-trans-4,5-trans-1-[3-(dimethylamino)propyl]-2-methyl-1,2,4,5-cyclohexanetetrol, tetraacetate ester. Recrystallization with Darco treatment from 125 ml of hexane gives, after standing at room temperature overnight, 1.8 g, mp 110°–112° C, which is dried at 80° C for 5 hrs over $P_2O_5$ and paraffin, 0.1 mm Hg..

EXAMPLE 4

1,2-trans-4,5-trans-1-[[[2-(Dimethylamino)ethyl]methylamino]methyl]-2-methyl-1,2,4,5-cyclohexanetetrol, tetraacetate ester To a solution of 25 g (0.245 moles) 93% trimethylethylenediamine in 100 ml pyridine stirring in an ice bath is added 38 g (0.245 moles) o-toluoyl chloride in 300 ml benzene. After standing at room temp for 60 hours the hydrochloride salt is filtered and washed with benzene. The solid is dissolved in water, basified with 10% sodium hydroxide and extracted with chloroform. The organics are dried (sodium sulfate) and evaporated. The sample is heated (100° C) under vacuum to yield 44 g (81%) N-[(2-dimethylamino)ethyl]N-methyl-o-toluamide.

The toluamide (44 g, 0.2 moles) is reduced with 8 g (0.2 moles) lithium aluminum hydride in 1 liter of ether to yield 40 g (97%) 2-[[[2-(dimethylamino)ethyl]methylamino]methyl]toluene.

A solution of the toluene amine (40 g, 0.194 moles) in 100 ml ether is added to 2.5 liters liquid ammonia. With stirring, 35 g (5 moles) lithium are added over ½ hr. This is allowed to stir for ½ hr and absolute ethanol added until the reaction mixture is white. The ammonia is evaporated. The residue is dissolved in water and extracted with ether. The organics are dried (potassium carbonate) and evaporated to yield 37 g (92%) 1-[[[2-(dimethylamino)ethyl]methylamino]methyl]-3,6-dihydrobenzene.

This dihydrobenzene (37 g, 0.178 moles) is dissolved in 330 ml 98% formic acid at 0° C. While stirring in an ice bath, 30.3 ml (0.338 moles) 70% perchloric acid are added dropwise over ½ hr. The mixture is allowed to warm to 20° C. With stirring, 44.5 ml (0.39 moles) 30% hydrogen peroxide are added over 1 hr (T ≤ 40°). The mixture is stirred overnight in a water bath. Water is added and the solution is evaporated. This procedure is repeated twice. The residue is cooled in an ice bath and 25% sodium hydroxide solution is added until the reaction solution is very basic of pH paper. Absolute ethanol (200 ml) is added and the solution refluxed for 1 hr, cooled to room temperature and extracted with ether. The organics are dried (magnesium sulfate) and evaporated. The aqueous layer is extracted with ethyl acetate. The organics are dried (magnesium sulfate) and evaporated. The two residues are combined and chromatographed on 550 g basic alumina, Activity III with 2 & 5% methanol in chloroform yielding 6.4 g (13%) 1,2-trans-4,5-trans-1-[[[2-(dimethylamino)ethyl]methylamino]methyl]-2-methyl-1,2,4,5-cycohexane tetrol.

The tetrol (6.4 g, 0.023 moles) is peracetylated in 97 ml acetic anhydride and 13.2 ml 70% perchloric acid to yield 3.8 g (37% crystalline tetraacetate ester.

Recrystallization of 3.8 g from hot hexane affords the analytical sample, 3.4 g, mp 85°–88° C.

EXAMPLE 5

1,2-trans-4,5-trans-2-Methyl-1-[(4-methyl-1-piperazinyl)methyl]-1,2,4,5-cycohexanetetrol, tetraacetate ester To a solution of 25 g (0.25 moles) N-methylpiperazine in 100 ml pyridine stirring at 0° C is added a solution of 38.7 g (0.25 moles) o-toluoyl chloride in 300 ml toluene over 45 mins. This is allowed to stand overnight. The hydrochloride salt is filtered and washed with benzene and ether. The solid is dissolved in water, basified with 10% sodium hydroxide and extracted with chloroform. The organics are dried (sodium sulfate) and evaporated. The pyridine is distilled off using vacuum (T = 100° C) to yield 38.2 g (70%) of N-methyl-N-(o-toluoyl)piperazine.

The toluoyl piperazine (38.2 g, 0.174 moles) is reduced with 7 g (0.174 moles) lithium aluminum hydride in 1 liter of ether to give a quantitative yield of N-methyl-N-(o-tolyl)piperazine.

The tolyl piperazine is subjected to Birch reduction in 2.5 liters liquid ammonia with 35 g (5 moles) of lithium to give a quantitative yield of crude N-methyl-N-(3,6-dihydro-2-methylbenzyl)piperazine.

The crude diene (35.9 g, 0.174 moles) is dissolved in 320 ml 98% formic acid at 0° C. With stirring, 29.6 ml (1.9 eq., 0.33 moles) 70% perchloric acid are added dropwise over ½ hr. This is allowed to warm to 20° and 43.5 ml (2.2 eq., 0.383 moles) 30% hydrogen peroxide are added dropwise over 1 hr (T ≤ 40° C). The mixture is stirred overnight in a water bath. The solution is evaporated. Water is added and evaporated twice. The flask is cooled at 0° C and 25% sodium hydroxide solution added until reaction is very basic to pH paper. Absolute ethanol (200 ml) is added and the reaction refluxed for 1 hr. The reaction is cooled to room temp and extracted with ether. The organics are dried (magnesium sulfate) and evaporated to yield 31 g crude product. The aqueous layer is extracted with ethyl acetate. These organics are dried and evaporated to yield 6.5 g of crude product. The crude products are combined and chromatographed on 600 g basic alumina, activity IV packed in chloroform. The sample is put on the column in 50% methanol in chloroform and the column eluted with 1methanol in chloroform. The second fraction from the column (8.9 g) is dissolved in ether and the crystals filtered (1 g). The mother liquor is evaporated and peracetylated in 120 ml acetic anhydride and 16.3 ml 70% perchloric acid. The crude product is dissolved in hot hexane and after standing for 3 days 1 g crystalline 1,2-trans-4,5-trans-2-methyl-1-[(4-methyl-1-piperazinyl)-methyl]-1,2,4,5-cyclohexanetetrol, tetraacetate ester is obtained.

Recrystallization of the tetraacetate from hot hexane-ethyl acetate affords the analytic sample. 0.8 g, mp 143°–145° C.

EXAMPLE 6

1,2-trans-4,5-trans-2-Methyl-1-[(1-methyl-4-piperidyl)-methyl]-1,2,4,5-cyclohexanetetrol A. 4-(α-Hydroxy-2-methylbenzyl)-N-methyl-piperidine A solution of 180 g (1.06 moles) of N-methyl-4-chloropiperidine hydrochloride in 300 ml of water is saturated with solid potassium carbonate and extracted with hexane. The organics are dried over magnesium sulfate for 2 hours and evaporated to give 106.7 g (0.79 mole) of the halide free base.

A mixture of 40 g (1.67 moles) of magnesium turnings and 200 ml of fresh tetrahydrofuran (THF) under nitrogen is reacted with 3 ml of ethylene dibromide (1,2-dibromoethane). When the reaction has subsided, 150 ml of a solution of halide (106.7 g) in 1 l. of THF is added. The mixture is then heated to a vigorous reflux and held there while the remaining halide is added over 1 hour. After an additional 15 minutes reflux the temperature is allowed to come to room temperature. Then a solution of 100 g (0.84 moles) of o-tolualdehyde in 500 ml of THF is added over ¼ hour at a rate which maintains the mixture just under reflux. After the addition is complete the mixture is refluxed for 1 hour, cooled in an ice bath and treated with enough saturated ammonium chloride to get two layers. The aqueous layer is reextracted with THF and the organics evaporated without drying. The oily product is taken up in ether and extracted with 10% hydrochloric acid. The aqueous layer is basified with 10% sodium hydroxide and extracted twice with ether. The layers are separated and benzene is added to the ether to remove water azeotropically on evaporation. The resulting slurry is triturated with hexane to give 105 g (60%) white solid adduct, mp 119°–123° C.

B. 4-(3,6-Dihydro-2-methylbenzyl)-N-methylpiperidine

A suspension of 21.5 g (0.1 mole) of the product from part A in 500 ml of liquid ammonia is treated with 60 ml of absolute ethanol, and then with 7 g (0.1 mole) of lithium over 25 minutes. After stirring 10 minutes longer, 30 ml of absolute ethanol is added to discharge the blue color. Ammonia is evaporated and enough water and ether added to dissolve all solids. The aqueous layer is reextracted with ether and the organics dried over potassium carbonate and evaporated. Hexane is added and evaporated to give 20.1 g (100%) crude diene. A sample is converted to the hydrochloride, mp 210°–215° C.

The crude diene (30.2 g, 0.147 moles) is dissolved in 250 ml 98% formic acid at 0° C. With stirring and cooling in an ice bath, 38.5 ml 30% hydrogen peroxide are added at once. The mixture is allowed to stir overnight. Water and sodium bisulfite are added until the solution gives a negative test to starch iodide paper. The solution is evaporated. The residue is dissolved in water-methanol and basified with potassium carbonate. The mixture is heated on the steam cone for ½ hr and after cooling to room temperature extracted with ethyl acetate. The organics are dried (magnesium sulfate) and evaporated to yield 16 g containing some tetrol.

The aqueous layer is extracted with n-butanol. The butanol is evaporated. Benzene-ethanol is added twice and evaporated. The residue is boiled in methanol-ethyl acetate and some salts filtered. Hexane is added to the filtrate. After standing overnight, crystalline (6.6 g, 16%) 1,2-trans-4,5-trans-2-methyl-1-[(1-methyl-4-piperidyl)methyl]-1,2,4,5-cyclohexanetetrol is separated by filtration.

Filtration of 2 g through a 50 g basic alumina, Activity IV, column in methanol and recystallization from methanol-ethyl acetate affords the analytical sample, 1.25 g, mp 192°–195°.

EXAMPLE 7

1,2-trans-4,5-trans-2-Methyl-1-[(1-methyl-4-piperidyl)methyl]-1,2,4,5-cyclohexanetetrol, tetraacetate ester A sample (4.6 g, 0.017 M) of the product of example 6 is peracetylated in 80 ml acetic anhydride and 4.1 ml 70% perchloric acid as described in example 1. This gives a quantitative yield of crude crystalline, 1,2-trans-4,5-trans-2-methyl-1-[(1-methyl-4-piperidyl)methyl]-1,2,4,5-cyclohexanetetrol, tetraacetate ester.

Recrystallization of the entire sample from ethyl acetate-hexane affords the analytical sample, 3.2 g, mp 162°–165° C.

EXAMPLE 8

1,2:4,5-trans-2-Methyl-1-[2-(1-methyl-4-piperidyl)-)ethyl]-1,2,4,5-cyclohexanetetrol, tetraacetate ester A mixture of 67 g (0.56 moles) of o-tolualdehyde, 52 g (0.56 moles) of $\gamma$ - picoline and 150 ml of acetic anhydride is refluxed under nitrogen for 24 hrs, then evaporated in vacuo. Water and 10% hydrochloric acid are added and the solution extracted with ether. The aqueous layer is basified with 10% sodium hydroxide and extracted with ether. Drying (potassium carbonate), evaporation, addition of benzene and another evaporation gives a black oil. Hexane (1 liter) is added, swirled vigorously and decanted to leave a black crystalline solid.

The above solid is taken up in 500 ml of acetonitrile and treated with 70 ml of methyl iodide. Warming at 40° C for 2 hrs, filtering, and washing the solid with acetonitrile gives 33 g dry orange solid, mp 216°–218° C. The mother liquors are diluted with 300 ml of ether to give 35 g dark solid, mp 180°–210° C, and these mother liquors further evaporated to give a small amount of black solid. The latter two solids are combined in a mixture of 1.5 liters of methanol and 0.5 liters of water and treated in portions with 25 g of sodium borohydride, maintaining T ≤ 40° C. The mixture is stirred 1 hr after the addition is complete, then diluted with 1 liter of water and extracted with ether. The organics are dried (potassium carbonate), evaporated, benzene added, and evaporated again to an oil. The oil is made up to 200 ml with ethyl acetate, 1.0 g of platinum oxide added, and hydrogenated overnight at 34 psi and 55° C. The filtered solution is evaporated to an oil which is distilled to yield 15 g (66%), bp 103°–105° C ε 0.05 mm Hg. A substantial residue remains in the still pot.

The above amine (15 g, 0.069 moles) is subjected to Birch reduction in 1 liter liquid ammonia with 13 g of lithium to give a quantitative yield of 2-methyl-1-[2-(1-methyl-4-piperidyl)ethyl]-3,6-dihydrobenzene.

The diene (15 g, 0.069 moles) at 0° C is dissolved in 117 ml 98% formic acid. While stirring at room temperature, 18 ml 30% hydrogen peroxide are added at once. This is allowed to stir in a water bath overnight. Water and sodium bisulfite are added until the solution is negative to starch iodide paper. The solution is evaporated. The residue is dissolved in methanol-water and basified with potassium carbonate. The mixture is heated on the steam cone for ½ hr, cooled to room temperature, and extracted with ether, ethyl acetate, and n-butanol. Each organic layer is dried separately (magnesium sulfate) and evaporated. Chromatography of the ethyl acetate and butanol residues (basic alumina, activity III, 5% methanol in chloroform) yields 9.85 g (50%) of 1,2:4,5-trans-2-methyl-1-[2-(1-methyl-4-piperidyl)ethyl]-1,2,4,5-cyclohexanetetrol.

The tetrol (8 g, 0.028 moles) is peracetylated in 135 ml acetic anhydride and 6.8 ml 70% perchloric acid to yield 6 g (48%) tetraacetate ester.

Recrystallization of 5.5 g of the tetraacetate from ethyl acetate-hexane affords the analytical sample 4.6 g, mp 119°–121° C.

EXAMPLE 9

3a,7a-trans-5,6-trans-Hexahydro-5-(3-piperidinopropyl)-3a,5,6,7a-indantetrol

A. 3-(5-Indanyl)-1-propanol

A solution of 20 g (0.11 M) of 5-indanacrylic acid (Aldrich) in 100 ml of dioxane is added dropwise to a suspension of 10 g of lithium aluminum hydride in 350 ml of ether. After an overnight reflux period, the mixture is decomposed with saturated $K_2CO_3$ solution, filtered, and the solvent removed in vacuo. Distillation affords 14.4 g (75%) of saturated alcohol boiling at 128°–133° (0.05 mm). NMR and IR indicates the absence of the double bond.

B. 3-(5-Indanyl)-1-bromopropane 3-(5-Indanyl)-1-propanol (14.4 g, 0.082 M) is dissolved in $CHCl_3$, cooled to 0–5° C, and treated dropwise with $PBr_3$ (10 g). The mixture is stirred, with cooling, for several hours and then poured into a cold dilute bicarbonate solution. The organic layer is dried and the solvent removed in vacuo leaving 13.0 g (66%) of crude halide. IR shows no OH.

C. 1-[3-(5-Indanyl)propyl]piperidine

The crude 3-(5-Indanyl)-1-bromopropane (13.0 g, 0.054 M) is dissolved in 200 ml toluene and treated with 50 g of piperidine. The mixture is heated under reflux overnight, then cooled and diluted with ether to precipitate salts. The salts are removed by filtration and the solvent removed from the filtrate in vacuo. The residue is distilled collecting 8.4 g (64%) of desired product boiling at 135°–140° (0.15 mm).

D. 4,7-Dihydro-1-[3-(5-indanyl)propyl]piperidine

A solution of 15 g (0.062 M) of distilled indanyl compound from C in 150 ml ether is added to 800 ml liquid ammonia. Lithium ribbon (15 g) is added in several portions over a period of 15 minutes. The mixture is stirred 30 minutes and then absolute ethanol is added dropwise until the color is discharged (225 ml added over a period of 90 minutes). The ammonia is evaporated, more ether is added and the mixture is diluted to 1½ liters with water. The layers are separated and the aqueous layer extracted one more time with ether. The combined organic layers are dried over $K_2CO_3$, filtered, and the solvent removed in vacuo leaving 15.0 g of crude diene (UV indicates <5% aromatic compound remaining).

E. 3a,7a-trans-5,6-trans-Hexahydro-5-(3-piperidinopropyl)-3a,5,6,7a-indantetrol

The crude diene (14.9 g, 0.061 M) is added dropwise to 110 ml of cold 88% formic acid. The solution is allowed to warm to 20° and held there while 30 ml of 30% hydrogen peroxide are added dropwise over a period of 1 hour. The temperature is then allowed to rise to about 35° and left stirring overnight in a water bath at room temperature. The reaction mixture is then taken to near dryness in vacuo. Residual performic acid is removed by 3 times adding water and removing in vacuo. The viscous residue is dissolved in 100 ml ethanol, a solution of 30 g KOH in 50 ml water is added, and the mixture is heated under reflux for 1 hour. After cooling the solution is diluted to 500 ml with water. Four ether extractions yield 15.7 g (84%) of brown viscous material. A small amount of ethyl acetate is added and on standing 7.5 g (40%) of crystalline material is deposited. A portion of this (2.5 g) is recrystalized from ethyl acetate to yield 1.9 g of title compound, mp 148°–151° C.

EXAMPLE 10

3a,7a-trans-5,6-trans-Hexahydro-5-(3-piperidinopropyl)-3a,5,6,7a-indantetrol, tetraacetate ester A sample of the final product from example 9 is acetylated following the procedure of the last paragraph of example 1 to yield the title compound, mp 198°–204° C.

EXAMPLE 11

1,2-trans-4,5-trans-1-[3-(Diethylamino)propyl]-2-methyl-1,2,4,5-cyclohexanetetrol, tetraacetate ester Following the procedure of example 3 but substituting for dimethylamine hydrochloride an equivalent amount of diethylamine hydrochloride, the title compound is obtained.

EXAMPLE 12

1,2-trans-4,5-trans-1-Methyl-2-(pyrrolidinyl)methyl-1,2,4,5-cyclohexanetetrol, tetraacetate ester Following the procedure of example 5 but substituting for N-methylpiperazine an equivalent amount of pyrrolidine, the title compound is obtained.

EXAMPLE 13

1,2-trans-4,5-trans-1-Methyl-2-(piperidinyl)methyl-1,2,4,5-cyclohexane tetrol, tetraacetate ester Following the procedure of example 5 but substituting for N-methylpiperazine an equivalent amount of piperidine, the title compound is obtained.

EXAMPLE 14

1,2:4,5-trans-1-Methyl-2-[2-(1-methyl-2-piperidyl)ethyl]-1,2,4,5-cyclohexanetetrol, tetraacetate ester Following the procedure of example 8 but substituting for γ-picoline an equivalent amount of α-picoline, the title compound is obtained.

EXAMPLE 15

1,2-trans-4,5-trans-1-[(1-Methyl-4-piperidyl)methyl]-2-methyl-1,2,4,5-cyclohexane tetrol, tetraacetate ester A solution of 20 g (0.1 mole) diene prepared as described in parts A and B of example 6 in 144 ml glacial acetic acid at 5° C is treated in three portions over 5 minutes with 15 g (0.105 mole) of 70% perchloric acid. To the solution of perchlorate at 15° C is added 47.7 g (0.25 mole) of 40% peracetic acid over 10 minutes maintaining the temperature at 35° C with an ice bath. After the addition is complete the bath is removed and the mixture maintained at 32° C temperature for 1 hour, then is heated at 40°–55° C for 2 hours. The heat is removed and replaced by an ice bath. When cold (5° C) the mixture is slowly diluted with 700 ml of ether, the oil allowed to settle, and the supernatant solution decanted. The oil is washed with 2 × 300 ml portions of ether, then covered with a blanket of nitrogen and cooled in a dry ice-acetone bath to −30° C. To this is added 250 ml of cold (5° C) acetic anhydride, followed by 2 ml of 70% perchloric acid. The mixture is stirred for 1 hour at −30° to 0° to dissolve all the oil, then cooled at −15° C overnight without stirring.

The stirred mixture in an ice-acetone bath at −10° C is treated with 120 ml of methanol at a rate to maintain the temperature at 10° C. After 30 minutes the temperature drops sharply as the last of the excess anhydride is consumed, and the mixture is poured into 500 ml of concentrated ammonium hydroxide cooled in an ice bath. This is then extracted with dichloromethane (1 l.), dried for 1 hour over magnesium sulfate, filtered and evaporated completely to a tan solid. Hexane (400 ml) is added and boiled and the solid is filtered, washed with hexane, and dried in air to give 20 g of solid. The hexane filtrates deposit another 1.3 g of crystalline solid.

The solids are combined and taken up in 500 ml of hot ethyl acetate cooled to 25° C and suction filtered through a dry pad of 350 g of Woelm neutral alumina, activity II, layered over with Celite. The filter cake is washed with another 500 ml of ethyl acetate. This filtration removes all of the colored impurities and affords single spot (TLC, neutral alumina, ethyl acetate, $r_f \cong .2$) tetraacetate. The ethyl acetate is evaporated completely, and the resulting solid swirled with 300 ml hexane, filtered and dried to give 14.6 g (33%) of tetraacetate, m.p. 162°–165° C.

EXAMPLE 16

1,2-trans-4,5-trans-1-[1-Methyl-3-pyrrolidinylethyl]-2-methyl-1,2,4,5-cyclohexanetetrol tetraacetate A. 1-Methyl-3-(2o-tolyl-2-hydroxyethyl)pyrrolidine A solution of 1.06 moles of 1-methyl-3-chloromethyl-pyrrolidine hydrochloride in 300 ml of water is saturated with solid potassium carbonate and extracted with hexane. The organics are dried over magnesium sulfate for 2 hours and evaporated to give 0.80 mole of the free base.

A mixture of 40 g (1.67 moles) of magnesium turnings and 200 ml of fresh THF under nitrogen in reacted with 3 ml of ethylene dibromide (1,2-dibromoethane). When the reaction has subsided, 150 ml of a solution of halide (0.80 mole) in 1 l. of THF is added. The mixture is then heated to a vigorous reflux and held there while the remaining halide is added over 1 hour. After an additional 15 minutes reflux the reaction is allowed to cool to room temperature. Then a solution of 100 g (0.84 moles) of o-tolualdehyde in 500 ml of THF is added over ½ hour at a rate which maintains the mixture just under reflux. After the addition is complete the mixture is refluxed for 1 hour, cooled in an ice bath and treated with enough saturated ammonium chloride to get two layers. The aqueous layer is reextracted with THF and the organics evaporated without drying. The oily product is taken up in ether and extracted with 10% hydrochloric acid. The aqueous layer is basified with 10% sodium hydroxide and extracted twice with ether. The layers are separated and benzene is added to the ether to remove water azeotropically on evaporation. The resulting slurry is triturated with hexane to give about 95 g white solid adduct.

B. 1-Methyl-3-[2-(3,6-dihydro-2-methylphenyl)-methyl]pyrrolidine

A suspension (0.1 mole) of the product from part A in 500 ml of liquid ammonia is treated with 60 ml of absolute ethanol, and then with 7 g (0.1 mole) of lithium over 25 minutes. After stirring 10 minutes longer, 30 ml of absolute ethanol is added to discharge the blue color. Ammonia is evaporated and enough water and ether added to dissolve all solids. The aqueous layer is reextracted with ether and the organics dried over potassium carbonate and evaporated. Hexane is added and evaporated to give about 20 g crude diene.

C. 1,2-trans-4,5-trans-1-[1-methyl-3-pyrrolidinyl-ethyl]2-methyl-1,2,4,5-cyclohexane tetrol tetraacetate A solution of diene (0.1 mole) from part B in 144 ml glacial acetic acid at 5° C is treated in three portions over 5 minutes with 15 g (0.105 mole) of 70% perchloric acid. To the solution of perchlorate at 15° C is added 47.7 g (0.25 mole) of 40% peracetic acid over 10 minutes maintaining the temperature at 35° C with an ice bath. After the addition is complete the bath is removed and the mixture maintained at 32° C temperature for 1 hour, then is heated at 40°-55° C for 2 hours. The heat is removed and replaced by an ice bath. When cold (5° C) the mixture is slowly diluted with 700 ml of ether, the oil allowed to settle, and the supernatant solution decanted. The oil is washed with 2 × 300 ml portions of ether, then covered with a blanket of nitrogen and cooled in a dry ice-acetone bath to −30° C. To this is added 250 ml of cold (5° C) acetic anhydride, followed by 2 ml of 70% perchloric acid. The mixture is stirred for 1 hour at −30° C to 0° C to dissolve all the oil, then cooled at −15° C overnight without stirring.

The stirred mixture in an ice-acetone bath at −10° C is treated with 120 ml of methanol at a rate to maintain the temperature at 10° C. After 30 minutes the temperature drops sharply as the last of the excess anhydride is consumed, and the mixture is poured into 500 ml of concentrated ammonium hydroxide cooled in an ice bath. This is then extracted with dichloromethane (1 l.) dried for 1 hour over magnesium sulfate, filtered and evaporated completely to a tan solid. This solid is triturated with 400 ml of hexane, filtered, and dried in air to give about 23 g of solid.

The solid is taken up in 500 ml of hot ethyl acetate cooled to 25° C and suction filtered through a dry pad of 350 g of Woelm neutral alumina, activity II, layered over with Celite. The filter cake is washed with another 500 ml of ethyl acetate. This filtration removes all of the colored impurities and affords single spot (TLC, neutral alumina, ethyl acetate, $r_f \cong .2$) tetraacetate. The ethyl acetate is evaporated completely, and the resulting solid swirled with 300 ml hexane, filtered and dried to give about 14.4 g (33%) of the title tetraacetate.

EXAMPLES 17 – 22

Following the procedure of example 3 but substituting for acetic-anhydride in the procedure described in the last paragraph of example 3, an equivalent amount of the anhydride listed in column I below, there is obtained the corresponding tetraester wherein each of $R^1$, $R^2$, $R^3$ and $R^4$ is as indicated in column II below:

| I | II |
|---|---|
| 17. propionic anhydride | propionyl |
| 18. trifluoroacetic anhydride | trifluoroacetyl |
| 19. dichloroacetic anhydride | dichloroacetyl |
| 20. monochloroacetic anhydride | monochloroacetyl |
| 21. monobromoacetic anhydride | monobromoacetyl |
| 22. β-iodopropionic anhydride | β-iodopropionyl |

EXAMPLE 23

A 2.3 g (0.008 mole) sample of the tetrol prepared according to the procedure of example 1 is dissolved in 40 ml pyridine. While cooling in an ice bath, acetic anhydride (1.8 ml) is added dropwise over a period of 30 minutes. After stirring overnight at room temperature, the mixture is taken to dryness in vacuo. The residue is dissolved in chloroform and extracted two times with 5% $K_2CO_3$ solution. The chloroform solution is dried over magnesium sulfate, filtered, and the chloroform is removed in vacuo. Benzene is added two times and removed in vacuo to free the sample of any residual pyridine. The products, a mixture of monoesters wherein $R^1$ and $R^3$ are acetylated, and a diester wherein both $R^1$ and $R^3$ are acetylated, are separated by column chromatography.

EXAMPLE 24

1,2-trans-4,5-trans-2-Methyl-1-[(1-methyl-3-pyrrolidyl)-ethyl]-1,2,4,5-cyclohexanetetrol A sample of 1-methyl-α-(2-methylphenyl)-3-pyrrolidine-ethanol (23 α, 0.105 moles) is subjected to Birch reduction in 500 ml liquid ammonia with 7 g (1 mole) of lithium to give a quantitative yield of 3-(3,6-dihydro-2-methylphenethyl)-N-methylpyrrolidine.

A sample of the diene (21 g, 0.105 moles) at 0° C is dissolved in 175 ml of 98% formic acid with stirring. The ice bath is removed and 28 ml of 30% hydrogen peroxide are added at once, and stirred overnight in a water bath. Water and sodium bisulfite are added until the solution gives a negative test to starch iodide paper. The solution is evaporated, water is added and evaporated again. The residue is dissolved in methanol, basified with 10% sodium hydroxide, and heated on the steam cone for ½ hour. After cooling, the solution (is extracted with ethyl acetate and n-butanol. The butanol organics are dried (magnesium sulfate), evaporated and chromatographed (100 g basic alumina, activity IV, 5% and 10% methanol in chloroform) to yield 3.8 g (13%) tetrol.

A sample, 0.5 g, is dried in vacuo overnight to afford the analytical sample 0.45 g, mp 118°-128° C.

EXAMPLE 25

1,2-trans-4,5-trans-1-Methyl-2-[(1-methyl-3-pyrrolidinyl)-ethyl]-1,2,4,5-cyclohexanetetrol tetraacetate A sample of the product of example 24 (2.7 g, 0.01 mole) is peracetylated as in example 1 to yield 3.5 g crystalline tetraacetate. Recrystallization from hot hexane affords the analytical sample, mp 90°-93° C.

EXAMPLE 26

1,2-trans-4,5-trans-1-[4-(Dimethylamino)butyl]-2-methyl-1,2,4,5-cyclohexanetetrol-tetrakis(ethylcarbonate)ester The product of example 2 (0.01 mole) is dissolved in pyridine(25 ml) in the cold and treated dropwise with 0.1 mole of ethylchlorocarbonate with stirring. After several hours the mixture is diluted with water, basified with ammonia, extracted into ether, dried and freed of solvent to yield the title compound.

EXAMPLE 27

1,2-trans-4,5-trans-2-Methyl-1-[(1-methyl-4-piperidyl)-methyl]1,2,4,5-cyclohexanetetrol-tetrakis(β-methoxypropionate)ester The product of example 6 (0.01 mole) is added to β-methoxypropionic anhydride (0.45 mole), cooled in dry ice-acetone, and treated with 3 ml of 70% perchloric acid. After standing overnight at −15° C, 60 ml of methanol are added over ½ hour with ice-acetone cooling. The mixture is poured into ice-ether-ammonia, the layers separated and the aqueous layer reextracted with ether. The organics are dried (magnesium sulfate) and treated with several portions of benzene with evaporation to dryness after each addition. The crude solid is taken up in 150 ml of hot hexane, treated with Darco, filtered hot and cooled to room temp. In 2 hours the solid is filtered and dried at 60° C, 0.1 mm Hg for 20 hours, over $P_2O_5$ and paraffin to give the title compound.

EXAMPLE 28

1,2-trans-4,5-trans-2-methyl-1-[(1-methyl-4-piperidyl)-methyl]-1,2,4,5-cyclohexanetetrol-tetrakis(benzyloxyacetate)ester Following the procedure of example 27 but substituting an equivalent amount of benzyloxyacetic acid anhydride for β-methoxy-propionic anhydride, the title compound is obtained.

EXAMPLE 29

1,2-trans-4,5-trans-1-[4-(Dimethylamino)butyl]-2-methyl-1,2,4,5-cyclohexanetetrol-tetrakis(benzyloxyacetate)ester Following the procedure of example 27 but substituting for β-methoxypropionic anhydride, an equivalent amount of benzyloxyacetyl chloride anhydride, and substituting an equivalent amount of the product of example 2 for the product of example 6, the title compound is obtained.

EXAMPLE 30

1,2-trans-4,5-trans-2-methyl-1-[(1-methyl-4-piperidyl)-methyl]-1,2,4,5-cyclohexanetetrol-tetrakis(N,N-dimethylglycinate)ester The product of example 6 (0.01 mole) is dissolved in pyridine (25 ml) in the cold and treated dropwise with 0.025 equivalents of chloroacetylchloride and the mixture is stirred at room temperature for 3 hours. Dimethylamine (0.2 equivalent) is added dropwise and stirred at room temperature for 3 hours, then warmed to 55° C for 1 hour. The mixture is then poured into ice extracted with ether, dried and freed of solvent to yield the title compound.

EXAMPLE 31

1,2-trans-4,5-trans-1-[4-(Dimethylamino)butyl]-2-methyl-1,2,4,5-cyclohexanetetrol-tetrakis(N-methylpiperazino acetate) ester The product of example 6 (0.01 mole) is dissolved in pyridine (25 ml) in the cold and treated dropwise with N-methylpiperazino acetic anhydride (0.2 equivalent). The mixture is stirred at room temperature for 3 hours, then warmed to 55° C for 1 hour. The mixture is then poured into ice, extracted with ether, dried and freed of solvent to yield the title compound.

EXAMPLE 32

1,2-trans-4,5-trans-2-Methyl-1-[(1-methyl-4-piperidyl)methyl]-1,2,4,5-cyclohexanetetrol-tetrakis(N-methylpyrrolidino acetate)ester Following the procedure of example 31 but substituting N-methylpyrrolidino acetic anhydride (0.2 equivalent) for N-methylpiperazino acetic anhydride and substituting the product of example 2 (0.01 mole) for the product of example 6, the title compound is obtained.

EXAMPLE 33

1,2-trans-4,5-trans-1-[4-(Dimethylamino)butyl]-2-methyl-1,2,4,5-cyclohexanetetrol-bis-4,5-(nicotinate)ester The product of example 2 (0.01 mole) is dissolved in pyridine (25 ml) and 2.2 equivalents of nicotinic anhydride are added. The mixture is stirred at room temperature for 3 hours, then heated for 3 hours to 55° C to complete the reaction. The reaction mixture is cooled, diluted with water, extracted into ether and dried. The title product is separated from the 4-(mono)nicotinate ester and the 5-(mono)nicotinate ester on a column of alumina.

EXAMPLE 34

1,2-trans-4,5-trans-2-Methyl-1-[(1-methyl-4-piperidyl)methyl]-1,2,4,5-cyclohexanetetrol-bis,4,5-(isonicotinate)ester Following the procedure of example 33 but substituting isonicotinic anhydride (2.2 equivalents) for nicotinic anhydride and substituting the product of example 6 for the product of example 2, the title compound is obtained.

EXAMPLE 35

1,2-trans-4,5-trans-2-Methyl-1-[(1-methyl-4-piperidyl)methyl]-1,2,4,5-cyclohexanetetrol-bis-4,5-(picolinate)ester Following the procedure of example 34 but substituting picolinic anhydride (2.2 equivalents) for isonicotinic anhydride, the title compound is obtained.

EXAMPLE 36

1,2-trans-4,5-trans-1-[4-(Dimethylamino)butyl]-2-methyl-1,2,4,5-cyclohexanetetrol-bis-4,5-(benzoate)ester The product of example 2 (0.01 mole) is dissolved in pyridine (25 ml) and 1.1 equivalents of benzoyl chloride are added. The mixture is stirred at room temperature for 3 hours, then diluted with water, extracted into ether and dried. The title product is separated from the 4-(mono)benzoate ester and the 5-(mono)benzoate ester on a column of alumina.

EXAMPLE 37

1,2-trans-4,5-trans-1-[4-(Dimethylamino)butyl]-2-methyl-1,2,4,5-cyclohexanetetrol-bis-4,5-(acryloate)ester Following the procedure of example 36 but substituting an equivalent amount of acryloyl chloride for benzoyl chloride, the title compound is obtained.

EXAMPLE 38

1,2-trans-4,5-trans-1-[4-(Dimethylamino)butyl]-2-methyl-1,2,4,5-cyclohexanetetrol-bis-4,5-(crotonoyl)ester Following the procedure of example 36 but substituting an equivalent amount of crotonoyl chloride for benzoyl chloride, the title compound is obtained.

EXAMPLE 39

1,2-trans-4,5-trans-1-[(1-Methyl-4-piperidyl)methyl]-1,2,4,5-cyclohexanetetrol-bis-4,5-(methacryloyl)ester The product of example 6 (0.01 mole) is dissolved in pyridine (25 ml) and 1.1 equivalents of methacryloyl chloride are added. The mixture is stirred at room temperature for 3 hours, then diluted with water, extracted into ether and dried. The title product is separated from the 4-(mono)methacryloate ester and the 5-(mono)methacryloate ester on a column of alumina.

EXAMPLE 40

1,2-trans-4,5-trans-1-[(1-Methyl-4-piperidyl)methyl]-1,2,4,5-cyclohexanetetrol-bis-4,5-(phenacetoyl)ester Following the procedure of example 39 but substituting an equivalent amount of phenacetyl chloride for acryloyl chloride, the title compound is obtained.

EXAMPLE 41

1,2-trans-4,5-trans-1-[4-(Dimethylamino)butyl]-2-methyl-1,2,4,5-cyclohexanetetrol-bis-4,5-(hydrocinnamoyl)ester Following the procedure of example 36 but substituting an equivalent amount of hydrocinnamoyl anhydride for benzoyl chloride, the title compound is obtained.

EXAMPLE 42

1,2-trans-4,5-trans-1-[4-(Dimethylamino)butyl]-2-methyl-1,2,4,5-cyclohexanetetrol-bis-4,5-(phenylbutyroyl)ester Following the procedure of example 36 but substituting an equivalent amount of phenylbutyroyl chloride for benzoyl chloride, the title compound is obtained.

EXAMPLE 43

| Preparation of capsule formulation | |
|---|---|
| Ingredient | Milligrams per Capsule |
| 1,2-trans-4,5-trans-2-Methyl-1-[(1-methyl-4-piperidyl)methyl]-1,2,4,5-cyclohexanetetrol, tetraacetate ester | 400 |
| Starch | 80 |
| Magnesium stearate | 5 |

The active ingredient, starch and magnesium stearate are blended together. The mixture is used to fill hard shell capsules of a suitable size at a fill weight of 485 milligrams per capsule.

EXAMPLE 44

| Preparation of tablet formulation | |
|---|---|
| Ingredient | Milligrams per Tablet |
| 3a,7a-trans-5,6-trans-Hexahydro-5-(3-piperidinopropyl)-3a,5,6,7a-indantetrol, tetraacetate ester | 100 |
| Lactose | 200 |
| Corn starch (for mix) | 50 |
| Corn starch (for paste) | 50 |
| Magnesium stearate | 6 |

The active ingredient, lactose and corn starch (for mix) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120° F. The dry granules are passed through a No. 16 screen. The mixture is lubricated with magnesium stearate and compressed into tablets in a suitable tableting machine. Each tablet contains 100 milligrams of active ingredient.

EXAMPLE 45

| Preparation of oral syrup formulation | |
|---|---|
| Ingredient | Amount |
| 1,2-trans-4,5-trans-1-[4-(Dimethylamino)-butyl]-2-methyl-1,2,4,5-cyclohexanetetrol, tetraacetate ester | 500 mg. |
| Sorbitol solution (70% N.F.) | 40 ml. |
| Sodium benzoate | 150 mg. |
| Sucaryl | 90 mg. |
| Saccharin | 10 mg. |
| Red Dye (F.D. & Co. No. 2) | 10 mg. |
| Cherry flavor | 50 mg. |
| Distilled water    qs to | 100 ml. |

The sorbitol solution is added to 40 milliliters of distilled water and the active ingredient is suspended therein. The sucaryl, saccharin, sodium benzoate, flavor and dye are added and dissolved in the above solution. The volume is adjusted to 100 milliliters with distilled water.

Other ingredients may replace those listed in the above formulation. For example, a suspending agent such as bentonite magma, tragacanth, carboxymethylcellulose, or methylcellulose may be used. Phosphates, citrates or tartrates may be added as buffers. Preservatives may include the parabens, sorbic acid and the like and other flavors and dyes may be used in place of those listed above.

What is claimed is:

1. A compound of the formula

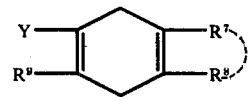

wherein

Y is a radical of the formula

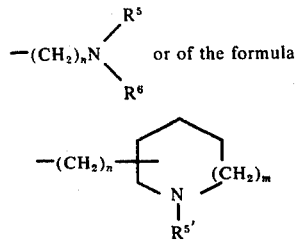

wherein $n$ is 1–6, $m$ is 0 or 1, $R^{5'}$ is hydrogen, alkyl of 1 to 3 carbons, or phenylalkyl containing 1 to 3 carbons in the alkyl group, and $R^5$ and $R^6$ together with the nitrogen to which they are attached are pyrrolidino, or piperidino;

$R^9$ is H, or a straight or branched chain alkyl radical of 1–6 carbon atoms;

$R^7$ and $R^8$ are the same or different and may be hydrogen or alkyl, or $R^7$ and $R^8$ taken together with the carbon atoms to which they are attached form a cycloalkyl ring having from 5 to 7 carbons.

2. A compound of the formula

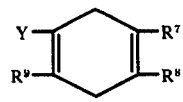

wherein
Y is a radical of the formula

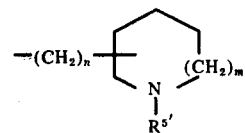

wherein $n$ is 1–6, $m$ is 0 or 1, and $R^{5'}$ is hydrogen, alkyl of 1 to 3 carbons, or phenylalkyl containing 1 to 3 carbons in the alkyl group;

$R^9$ is H or a straight or branched chain alkyl radical of 1–6 carbon atoms; and $R^7$ and $R^8$ are the same or different and are hydrogen or alkyl of 1–4 carbon atoms.

3. A compound as defined in claim 2 having the name 4-(3,6-dihydro-2-methylbenzyl)-N-methylpiperidine.

4. A compound as defined in claim 2 having the name 2-methyl-1-[2-(1-methyl-4-piperidyl)ethyl]-3,6-dihydrobenzene.

5. A compound as defined in claim 2 having the name 1-methyl-3-[2-(3,6-dihydro-2-methylphenyl)methyl]-pyrrolidine.

6. A compound as defined in claim 2 having the name 3-(3,6-dihydro-2-methylphenethyl)-N-methylpyrrolidine.

* * * * *

UNITED STATES PATENT AND TRADEMARK OFFICE
CERTIFICATE OF CORRECTION

PATENT NO. : 4,033,971

DATED : July 5, 1977

INVENTOR(S) : Frederic Peter Hauck et al.

It is certified that error appears in the above—identified patent and that said Letters Patent are hereby corrected as shown below:

On the Abstract page, Column 2, line 3 after the first two formulas, "$R^5$ is hydrogen" should read --$R^{5'}$ is hydrogen--.
Column 2, line 27, "g" should read --q--.
Column 3, line 5, second formula, "$R^5$" should read --$R^{5'}$--.
Column 3, line 9, before "$R^5$ and $R^6$" insert --$R^{5'}$,--.
Column 5, line 66, "from" should read --form--.
Column 8, line 9, "chromatography" should read --Chromatography--.
Column 9, line 1, "of" should read --to--.
Column 9, line 15, after "(37%" insert --)--.
Column 9, line 62, after "1" insert --%--.
Column 10, line 29, "1/4" should read --1/2--.
Column 11, line 30, ")ethyl" should read --ethyl--.
Column 14, line 46, "2o" should read --2-o--.

Signed and Sealed this

Twenty-fifth Day of October 1977

[SEAL]

Attest:

RUTH C. MASON
Attesting Officer

LUTRELLE F. PARKER
Acting Commissioner of Patents and Trademarks